United States Patent [19]

Sutter

[11] Patent Number: 4,553,942

[45] Date of Patent: Nov. 19, 1985

[54] DEVICE INCLUDING A SCREW PIN AND A DRIVEN MEMBER FOR SCREWING THE PIN INTO A TOOTH

[75] Inventor: Franz Sutter, Niederdorf, Switzerland

[73] Assignee: Institute Straumann AG, Waldenberg, Switzerland

[21] Appl. No.: 671,695

[22] Filed: Nov. 15, 1984

[30] Foreign Application Priority Data

Nov. 17, 1983 [CH] Switzerland .................... 6183/83

[51] Int. Cl.⁴ .............................................. A61C 5/04
[52] U.S. Cl. .................................................... 433/225
[58] Field of Search ..................... 433/225; 81/436; 44/402, 403, 407, 410

[56] References Cited

U.S. PATENT DOCUMENTS 3,434,209  3/1969  Weissman ......................... 433/225
4,449,937  5/1984  Weissman ......................... 433/225

Primary Examiner—Robert Peshock
Attorney, Agent, or Firm—Toren, McGeady, Stanger, Goldberg & Kiel

[57] ABSTRACT

An axially extending screw pin to be screwed into a tooth has a threaded part and an engagement part with a slot in one end. The slot extends in the axial direction of the pin toward the threaded part with the axially extending surfaces of the slot converging inwardly toward its base which has a concave, semi-circular surface. The converging sides are convex surfaces defining a quarter arc of a circle. A driven member with an engagement projection at one end shaped complementary to the slot, is disengageably connectible with the screw pin. A gripping member is axially displaceable positioned on the engagement projection end of the driven member. The gripping member is freely rotatable relative to the driven member and has resilient gripping tongues for holding a screw pin relative to the driven member. The driven member is mounted in a drive member so that is can be rotated about its axis. With the screw pin held by the gripping member, the engagement projection is inserted into the slot and threads the screw pin into a tooth. When a stop on the screw pin engages the tooth after it has been driven in for a given depth, the engagement projection backs out of the slot discontinuing the driving action.

24 Claims, 11 Drawing Figures

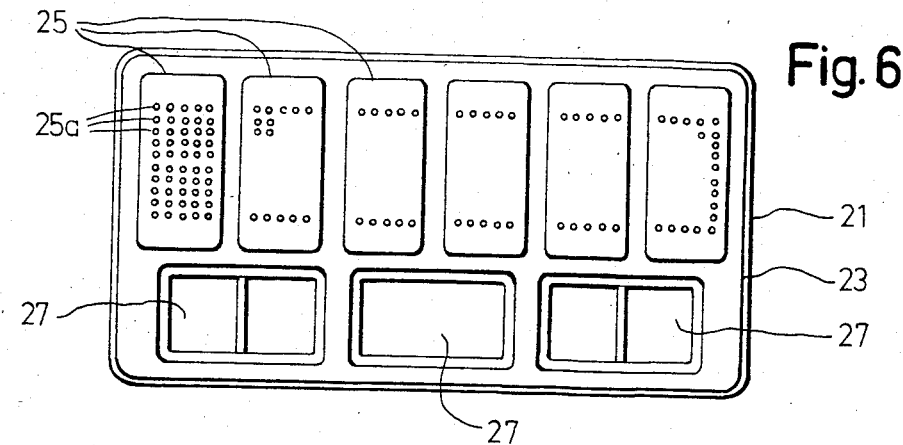
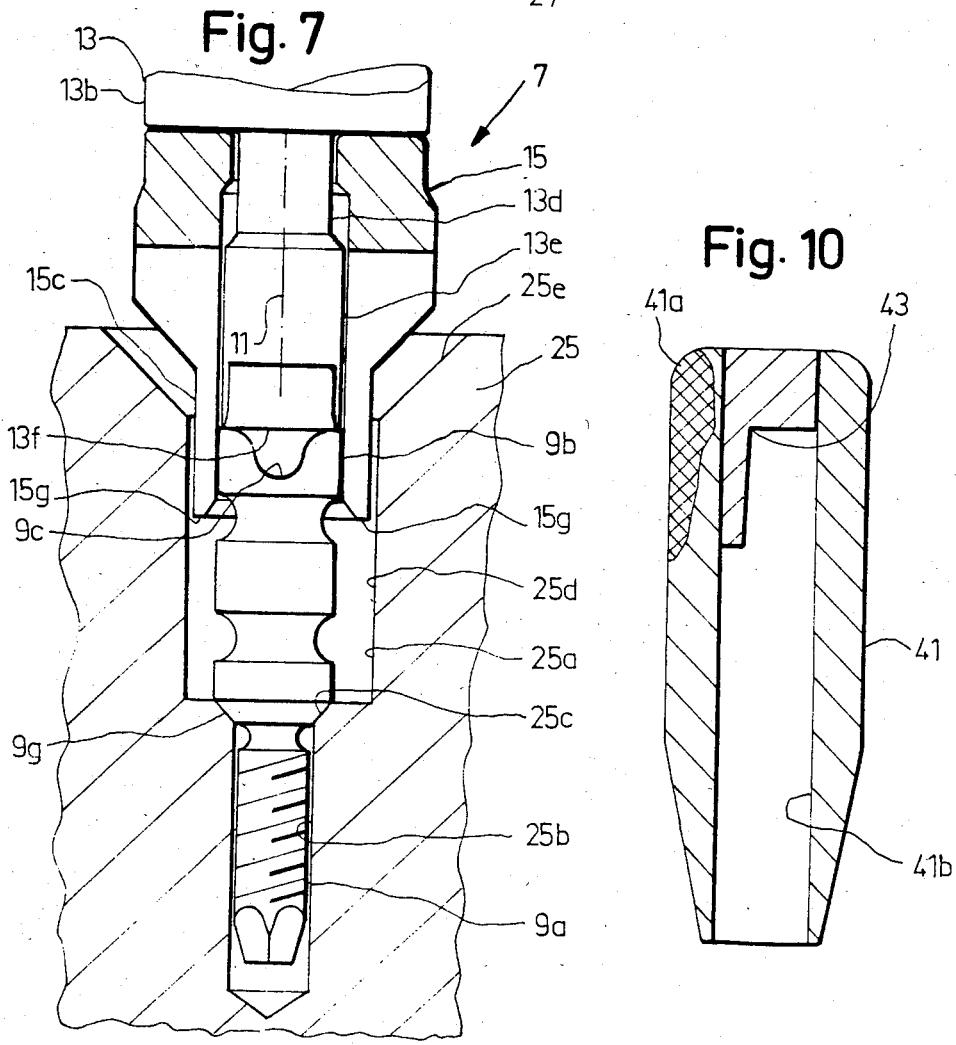

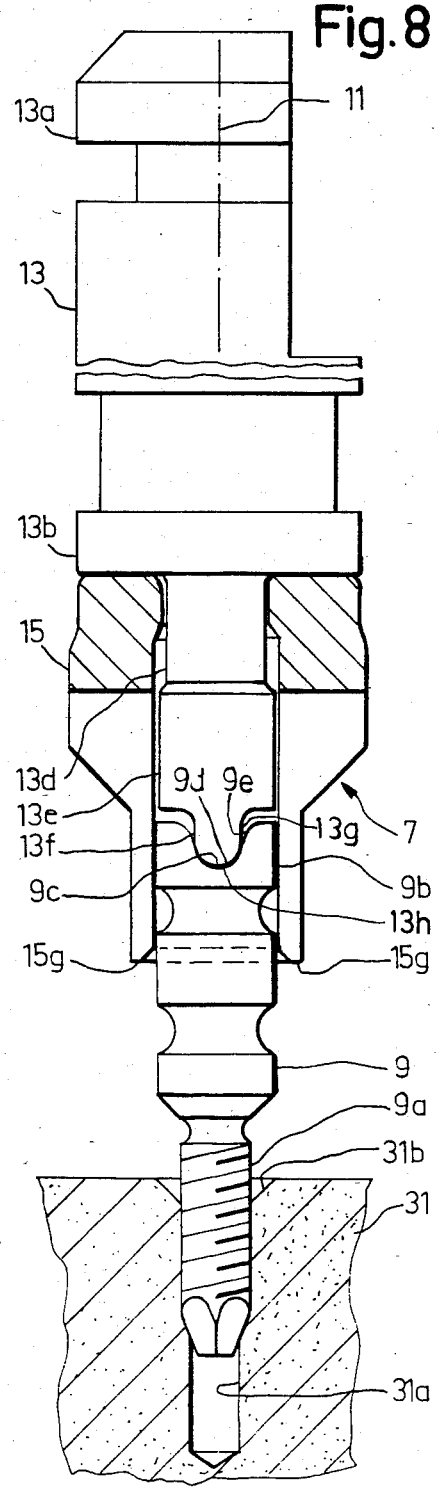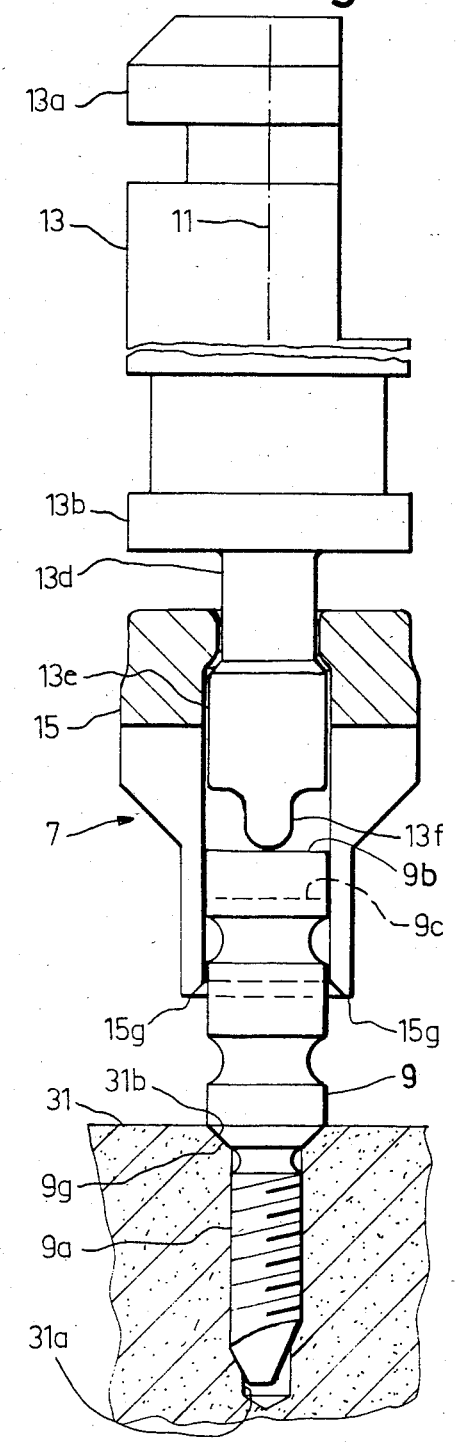

DEVICE INCLUDING A SCREW PIN AND A DRIVEN MEMBER FOR SCREWING THE PIN INTO A TOOTH

BACKGROUND OF THE INVENTION

The present invention is directed to an assembly including an axially elongated screw pin arranged to be screwed into a tooth. The screw pin has an axially extending threaded part followed by an axially extending engagement part. A driven member is engageable with the engagement part for driving the threaded part of the screw pin into a tooth. The driven member and the engagement part are arranged so that the driven member is disengaged from the screw pin when the pin is fixed in the tooth.

Known parapulpal or dentine screw pins are screwed into the dentine portion of the tooth, that is, the portion of the tooth completely outside the pulp. Such pins have a threaded part and an engagement part which can be temporarily held by a gripping member. The gripping member includes a rod-like part which at one end can be detachably connected with the angle piece of a dental drill and the other end contains a hole or slot in which the engagement part can be gripped. An annular notch or groove is provided between the threaded part and the engagement part which forms a predetermined breaking point.

When such a dentine screw pin is to be inserted, initially a borehole is drilled in the tooth. Next, a pin is removed from a screw pin supply container using forceps or the like and the pin is inserted into the gripping member positioned in the angle piece of a dental drill. Next, the screw pin is mechanically screwed into the borehole using the dental drill as the drilling or driving member. When the screw pin is fixed in the tooth it breaks off at the annular groove. The threaded part and a head part, possibly formed as a portion of the threaded part, remains in the tooth while the engagement part of the pin remains in the gripping member.

Accordingly, in such a screw pin the engagement part is separated from the threaded part which remains in the tooth so that there is a material loss which results in increased costs. Another disadvantage is that the engagement part must be removed from the gripping device in a separate operation and the insertion of the screw pin in the gripping member is a relatively time-consuming operation. These various operations are made more difficult because of the small dimensions of the screw pin where the threaded part has a maximum diameter of about 1 mm and is usually in the range of 0.35 to 0.8 mm.

Further, there are known screw pins each having two threaded parts and two annular grooves each forming a predetermined breaking point. One of the annular grooves is located between the engagement part and the threaded part and the other is arranged between the two threaded parts. With this construction, the front threaded part is screwed into the borehole in a tooth so that the threaded part fixed in the tooth breaks off from the screw pin at the location between the two threaded parts. Subsequently, the rear threaded part is fixed into another borehole and it breaks off from the engagement part at the annular groove between them. With this screw pin construction, the material loss is reduced relative to the screw pins described above which have only one threaded part. Screw pins with two threaded parts, however, have the disadvantage that they are more difficult to handle because of the original greater length. Moreover, it is possible in the screwing-in operation that the screw pin may break off between the rear threaded part and the engagement part instead of between the two threaded parts so that the rear threaded part must be separated from the front threaded part and it can no longer be used resulting in a loss of material.

SUMMARY OF THE INVENTION

Therefore, the primary object of the present invention is to provide an assembly in which a screw pin to be threaded into a tooth is automatically separated from a driven device after it has reached a predetermined depth in the tooth without requiring any separation of the screw pin along its length.

In accordance with the present invention, the screw pin is provided with a threaded part followed by an engagement part. A driven member is engageable within a notch in the rear end of the engagement part so that when the threaded part is screwed in for a predetermined depth the driving connection between the screw pin and the driven member is discontinued. A number of advantageous features of the present invention are set forth in the description and claims which follows.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWING

In the drawing:

FIG. 6 is a plan view of a container for holding the screw pins with the container cover removed;

FIG. 7 is an elevational view shown partly in section illustrating the container with a screw pin located within the container and a portion of the driven device including a gripping member illustrated on the same scale as used in FIGS. 2–4;

FIG. 8 is an elevational view, partly in section, showing a portion of a tooth, the driven member and the gripping member in position for inserting a screw pin into the tooth;

FIG. 9 is a view similar to FIG. 8, however, the screw pin is completely inserted into the tooth and the engagement projection on the driven member is disengaged from the engagement part of the screw pin;

FIG. 10 is a sectional view through a handle; and

DETAILED DESCRIPTION OF THE INVENTION

Figure 1:
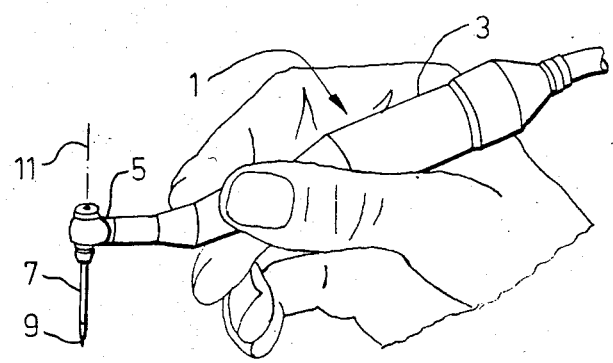
FIG. 1 is a perspective view illustrating an assembly including a drive device, a driven part, and a screw pin mounted in the driven part.

As shown in FIG. 1 a drive member 1 includes a motor 3 and an angle piece 5 containing a gear unit and the drive member 1 can be a conventional dental drill. As shown, the drive member 1 is held in a person's hand. The angle piece 5 contains a conventional snap bolt lock for releasably fastening a driven member 7 in the angle piece. A screw pin 9 is secured on the driven member 7 so that it can be released from the driven member. The drive member 1 can rotate the driven member 7 and the screw pin 9 around a rotational axis 11 when the motor 3 in the drive member is operated. The driven member 7 and the screw pin 9 are generally rotationally symmetrical relative to their longitudinal axes which coincide with the rotational axis 11 as shown in FIG. 1.

For the purpose of this description, as viewed in the drawing, the lower end of the screw pin 9 and the driven member 7 are the front ends and the upper ends are the rear ends.

Figure 2:
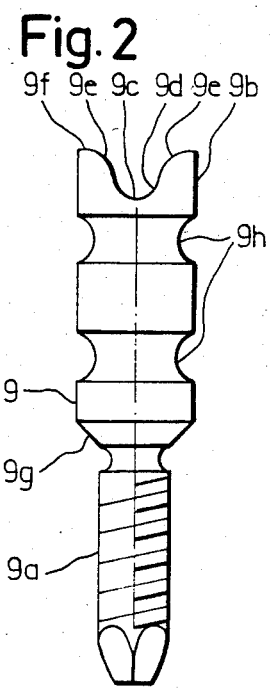
FIG. 2 is an elevational view of a screw pin shown on an enlarged scale.
Figure 5:
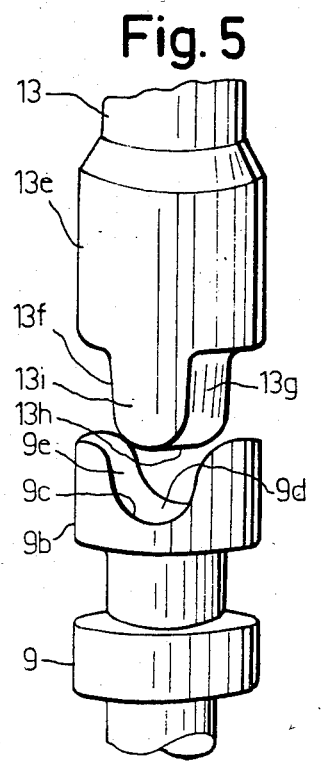
FIG. 5 is a perspective view of the engagement part of the screw pin and the engagement projection of the rod-like member of the driven member shown on an enlarged scale as compared to FIGS. 2 and 4 with only an axial portion of the screw pin illustrated.
Figure 3:
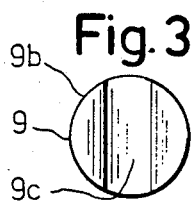
FIG. 3 is a plan view of the upper end of the engagement part of the screw pin as shown in FIG. 2.

The screw pin 9 shown in FIGS. 2 and 3 and illustrated partially in FIG. 5, is formed of metal, such as a rust-resistant steel, and includes a threaded part 9a extending from the front end toward the rear end and an engagement part 9b extending from the rear end to the threaded part 9a remote from the front end. The screw pin 9 is detachably secured at its rear end in the front end of the driven member 7. The thread on the threaded part 9a is preferably formed so that it is self-tapping and the front end of the threaded part is provided with at least one ground surface inclined relative to the rotational axis 11 for improving the cutting characteristic of the pin at the front end of the thread, for example the front end is provided with three such surfaces forming the frustum of a pyramid.

The rear end of the screw pin, that is, the rear end of the engagement part 9b, is provided with a notch or slot 9c and the slot extends diametrically across the engagement part and is open at its diametrically opposite ends located in the outer circumferential surface of the engagement part. In the elevational view displayed in FIG. 2 and, as a result, in the axial section along the screw pin-rotational axis 11, which section is parallel with the plane of FIG. 2, the axially extending side surfaces of the slot 9c converge inwardly from the rear end of the engagement part to the base of the slot. As a result, the slot narrows continuously from the rear end to the base of the slot. The base of the slot 9c is defined by a base surface 9d which is concave in the axial section parallel to the plane of FIG. 2. The opposite sides of the slot 9c are formed by side surfaces 9e with a convex curvature in the above-named axial section. The side surfaces 9e extend continuously from the concave base surface 9d into the radial rear end face 9f of the engagement part and the rear end face is disposed perpendicularly to the rotational axis 11. The concave base surface 9d extends along a circular arc with a maximum of 180°, that is, exactly 180°, and the two convex side surfaces 9e each extends along a circular arc of a maximum of 90°, that is, exactly 90°. The radius of curvature of the two side surfaces 9e is preferably at least approximately equal to the radius of curvature of the base surface 9d. The outer circumferential surface of the engagement part 9b is cylindrically shaped and has a larger diameter than the threaded part 9a. At the rear end of the threaded part 9a, that is, the transition from the threaded part to the engagement part, there is an annular conically shaped stop face 9g spaced from the end of the thread by an annular groove. The stop face 9g extends radially outwardly from the rear end of the threaded part 9a and widens in the direction toward the rear end of the screw pin 9. Between the stop face 9g and the rear end 9f, the engagement part 9b has at least one annular groove 9h dividing the cylindrically shaped circumferential surface of the engagement part into axially spaced sections. In fact, in FIG. 2 the engagement part 9b has two annular grooves 9h.

Screw pin 9, as mentioned above, may be a so-called parapulpal or dentine screw pin which is inserted into a live tooth parapulpally, that is, completely outside the pulp of the tooth. The smallest diameter of the threaded part 9a is about 0.3 mm and the maximum diameter is about 1 mm and, by way of example, the diameter is in the range of approximately 0.4 to 0.9 mm. As can be noted in FIG. 2, the outside diameter of the engagement part 9b is preferably 0.3 to 0.5 mm greater than the diameter of the threaded part and the radius of curvature of the base surface 9d and of the side surfaces 9e can fall within the range of 0.1 to 0.3 mm. The length of the threaded part 9a is approximately 1.5 to 2.5 mm and the length of the engagement part 9b is approximately 1.5 to 3.5 mm.

Figure 4:
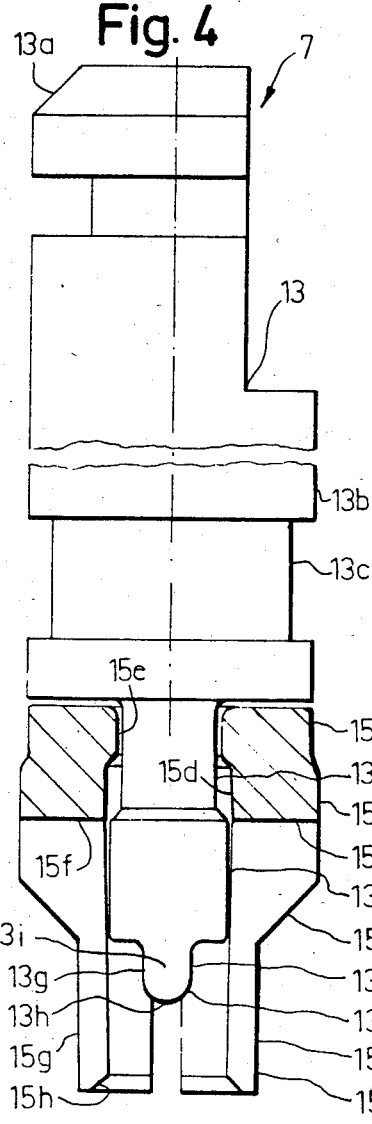
FIG. 4 is a view, partly in axial section, through the driven member illustrated on the same scale as used in FIG. 2 with the rod-like member of the driven member shown in an elevational view.

Driven member 7, shown alone in FIG. 4, includes a monolithic metallic rod-like member 13 formed of rust-resistant steel and including a rear end section 13a which is shaped to provide a detachably connectable coupling with the snap bolt block of the angle piece 5. Extending axially from the rear end section 13a is a cylindrically shaped section 13b with an annular marking groove 13c extending circumferentially around the section 13b and provided with an identification color. The front end of the cylindrically shaped section 13b is connected to an axially extending reduced diameter section 13d with a plug-like cylindrical section 13e extending toward the front end of the driven member. The plug-like section 13e has a diameter smaller than that of the cylindrically shaped section 13b. The reduced diameter plug-like section 13e has a front end face from which an engagement section 13f projects in the axial direction. The engagement section 13f forms the front end of the rod-shaped member 13 and is also shown in perspective in FIG. 5. The engagement section or projection 13f extends across a diameter of the front end of the reduced cylindrical section 13e and the rear end of the engagement projection is formed as a unit with the plug-like section 13e. The width of the rear end of the engagement projection 13f, apart from the rounded fillets forming the transition of the front end of the section 13e, is defined by a pair of planar side surfaces 13g which are parallel to one another and to the rotational axis 11 of the driven member 7. The front end of the engagement projection 13f is formed by a continuously narrowing section as can be seen in the elevational view in FIG. 4. The front end of the expansion projection 13f is convexly shaped and forms a semi-circular front end face 13h which merges continuously into the two side surfaces 13g. While the side surfaces 13g form the wider side of the engagement projection 13f the narrower sides 13i are defined by extensions of the cylindrical surface of the section 13e, in other words they are located in a circular arc extending around the rotational axis 11. As can be seen in FIG. 5, the narrower side surfaces 13*i* form a continuation, in the axial direction, of the outside surface of the reduced diameter section 13*e*.

Preferably, the diameter of the reduced diameter section 13*e* of the rod-shaped member 13 is somewhat smaller than the diameter of the engagement part 9*b* of the screw pin 9. The radius of curvature of the front end face 13*h* of the member 13 is preferably approximately equal to the radius of curvature of the base surface 9*d* in the slot 9*c* in the rear end of the screw pin, so that the engagement projection 13*f* can fit closely or with a slight play in the base surface 9*d* of the slot 9*c* in the screw pin 9. The thickness of the engagement projection 13*f*, that is, the distance between the wider side surfaces 13*g* is equal to twice the radius of the front end face 13*h* and is approximately 30 to 50% of the diameter of the engagement part 9*b*.

The driven member 7 includes a unitary gripping member 15 which is freely rotatably mounted on the portion of the rod-shaped member 13 in the region of the reduced diameter section 13*d* and the plug-like section 13*e* from which the engagement projection extends axially. Further, the gripping member is axially displaceably mounted on the rod-shaped member 13. The gripping member 15 is formed of metal, such as a rust-resistant steel, and is generally sleeve-like and serves as a chuck for an axially extending section from its front end toward its rear end. Starting at its rear end, the gripping member 15 has a substantially cylindrical main end section 15*a* preceded by a conically shaped section 15*b* converging inwardly toward the front end of the gripping member and a smaller diameter cylindrical front end section 15*c* terminating at the front end of the gripping member. The front end section 15*c* has reduced thickness walls as compared with the walls of the main section 15*a* and the conically shaped section 15*b*. A coaxial opening or bore 15*d* extends from the front end to the rear end of the gripping member 15. After the main section 15*a* of the gripping member 15 is placed onto the rod-shaped member 13 the rear end of the gripping member is deformed in the radially inward direction about the reduced diameter cylindrical section 13*d* forming an axially extending end part 15*e* with a smaller inside and outside diameter. Accordingly, the rear end of the gripping member 15 projects inwardly in the end part 15*e* of the bore 15*d* so that it is in closely fitting sliding relationship in the axial direction with the reduced diameter cylindrical section 13*d*. As a result, the front end of the cylindrically shaped section 13*b* and the rear end of the plug-like section 13*e*, which end surfaces face one another, form stops limiting the axial displacement of the gripping member 15 in the axial direction of the rod-like member 13. The gripping member can be displaced in the axial direction for a dimension approximately equal to the depth of the slot 9*c* in the rear end of the screw pin 9. The reduced thickness front end section 15*c* of the gripping member 15 is also in axially displaceable relation with the front end of the rod-like member 13 and projects beyond the front end of the engagement projection in the different axially displaceable positions of the gripping member 15.

At its front end, the gripping member 15 is provided with slots 15*f* at spaced locations around its circumference and in parallel relation with its axis of rotation, with the slots extending from the front end of the gripping member along the length of the front end section 15*c* through the conically shaped section 15*b* and partly into the main section 15*a*. As a result, the slots 15*f* divide the front part of the gripping member into a plurality of tongues 15*g*, for instance, four such tongues. During the production of the gripping member 15, the tongues 15*g* are deformed inwardly so that the inner surfaces of the tongues, which initially form a cylindrical surface, and the outer surfaces of the tongues converge inwardly toward the rotational axis 11 of the driven member 7, that is, toward the free end of the tongues. The gripping member 15 is hardened during or after the inward deformation of the tongue 15*g* so that the tongues have a good elasticity. The front or free ends of the tongues 16*g* are chamfered on their inner surfaces 15*h* so that the surfaces widen toward the front end of the gripping member. As a result, the entrance into the bore 15*d* has a conically shaped lead in surface facilitating the entry of the engagement part 9*b* of the screw pin 9 into the gripping member between the tongues when the screw pin is gripped by the member. At the narrowest point of the entrance into the bore 15*d* at the front end of the gripping member 15, the diameter is slightly smaller than the outside diameter of the engagement part 9*b*. Accordingly, it is possible for the resilient tongues 15*g* to grip and lightly hold the engagement part 9*b* of the screw pin 9 so that the screw pin does not fall, due to its own weight, out of the gripping member, and can be easily removed from the gripping member.

In FIG. 6 the lower part of a container 21 is illustrated with its cover removed and an insert fitted into the container. The insert 23 contains a number of screw pin carriers 25 each having a number of vertical holes 25*a* with each hole arranged to receive and hold a screw pin 9. As shown in FIG. 6, the container has six carriers or supports 25 and each carrier can hold a different sized screw pin. Each carrier is provided with a symbol designating the type of screw pin it holds. For example, the screw pins could be formed with different thread diameters such as 0.6 or 0.8 mm and different diameters of 1 or 1.2 mm. Further, the different sized screw pins could also be provided with different lengths of the engagement part, such as 1.5 mm, 2.5 mm and 3.5 mm, so that these different length engagement parts have a different number of annular grooves ranging from one annular groove to the two annular grooves 9*h* shown in FIG. 2 to three annular grooves. Furthermore, several compartments 27 are provided in the container 21 for holding driven members 7, drills and other components.

One of the holes 25*a* is shown in vertical section in FIG. 7 and the hole is stepped inwardly so that the lower hole section 25*b* has the smallest diameter and is dimensioned for receiving the threaded part 9*a* of a screw pin so that the threaded part fits closely or with a slight radial play in the hole section. Extending upwardly from the upper end of the hole section 25*b* is a conically widening hole section 25*c* adapted to support the conical stop face 9*g* on the screw pin 9. An upper cylindrical hole section 25*d* extends upwardly from the conical section 25*c* and has a diameter greater than that of the lower hole section 25*b* and larger than the outside diameter of the engagement part 9*b* of the screw pin and also larger than the outside diameter of the front end section 15*c* of the gripping member 15. The axial length of the upper hole section 25*d* is approximately equal to the length of the engagement part 9*b*. Extending upwardly from the upper end of the upper hole section 25*d* is an upwardly conically widening entrance section 25e. The holes 25a of each carrier 25 are constructed identically and the holes in the different carriers have different dimensions according to the dimensions of the screw pins to be inserted into them.

Now the use of the assembly of the driven member 7 and the screw pin 9 will be explained when a tooth 31, note FIGS. 8 and 9, is to be repaired. Initially, the dentist drills a hole 31a into the tooth for each screw pin 9 to be inserted and each hole 31a has a conically shaped countersunk entrance 31b. The drilled hole 31a is a blind hole or bore and does not extend into the portion of the tooth containing the pulp. To drill such a hole 31a, it is advisable to use a drill having a cylindrical part for drilling the main cylindrical section of the hole 31a and a conical part for forming the countersunk entrance 31b to the hole. Such a drill can be inserted into the angle piece 5 of the drill or drive device 1.

After the hole 31a is completed and the drill removed from the angle piece, a driven member 7 is placed in the angle piece 5. With the dentist holding the drive device 1 as shown in FIG. 1, the driven member can be inserted into a hole 25a in one of the carriers 25 in the container 21 holding a screw pin 9 of the desired type and size and this operation is carried out when the driven member is not being rotated. The conical entrance 25e to the hole 25a guides and centers the gripping member 15 on the driven member 7 so that it moves to the position shown in FIG. 7 without any difficulty. As a result, the rear end of the gripping member 15 is moved axially along the reduced diameter cylindrical section 13d and contacts the stop surface formed by the front end face of the upper cylindrically shaped section 13b so that the free or front ends of the tongues 15 grasp the rear end section of the engagement part 9b and hold it. During this operation, the tongues 15 are lightly and resiliently displaced outwardly from one another so that the inside surface formed by the tongues, which originally is slightly inclined inwardly toward the rotational axis, now extends aporoximately parallel to the rotational axis and lightly holds the engagement part 9b. During this operation the engagement projection 13f can move into the notch 9c in the screw pin engagement part or, as shown in FIG. 7, the front end face 13h can be placed in contact with the rear end face 9f of the screw pin. With the screw pin 9 held by the gripping member 15 on the driven member 7, the pin can be lifted out of the hole 25a by moving the drive device 1 upwardly and the pin can then be inserted into the countersunk entrance 31b to the hole 31a drilled in the tooth 31, note FIG. 8. With the front end of the screw pin positioned within the hole 31a, the drive device 1 is placed in operation and by pressing the screw pin into the hole in the tooth the pin is screwed into the hole by exerting a light force by hand on the drive device. The engagement projection 13f on the driven member 7 moves into the slot 9c so that the rod-shaped member 13 of the driven member is non-rotatable relative to the screw pin and the gripping member 15 is displaced axially relative to the screw pin toward the front end of the pin. When the front end of the engagement projection 13f is engaged securely or with a slight play in the base section 9d an open intermediate space is formed between the two side surfaces 13g of the engagement projection 13f and the convexly curved side surfaces 9e in the slot 9c. When the engagement projection 13f is seated within the slot 9c of the screw pin 9 in this manner, the rod-shaped member 13 driven by the drive device 1 rotates the screw pin and transmits a torque to the pin so that the screw pin is threaded into the hole 31 in the tooth to the position as shown in FIG. 8.

When the screw pin 9 is screwed into the hole 31a for the desired depth and its conical stop face 9g moves into contacting engagement with the conical countersunk entrance 31b of the hole 31a, the rotational movement of the screw pin is braked so that it comes to a stop. The increase in the braking action retarding the transmission of torque from the rod-like member to the screw pin causes the engagement projection 13f to be displaced out of the slot 9c in the direction away from the threaded part 9a so that the rod-shaped member 13 naturally moves away from the screw pin 9. As a result, the coupling between the rod-shaped member 13 and the screw pin is interrupted and the rod-shaped member can continue to rotate when the insertion of the screw pin is completed until the dentist separates the drive device 1 and the driven member 7 from the screw pin and/or turns off the drive device. At least during the uncoupling of the engagement projection 13f out of the slot 9c, the gripping member 15 holds the screw pin as the rod-shaped member rotates and the screw pin is stopped whereby the rod-shaped member 13 rotates relative to the gripping member 15 during this operation. During the uncoupling operation, however, the rod-shaped member 13 can be displaced axially relative to the gripping member 15 so that the gripping member does not have to be displaced relative to the screw pin 9. This feature avoids scratching or other damage to the circumferential surface of the engagement part of the screw pin during the uncoupling operation.

Thus, the assembly in combination with the drive device enables a dentist or other person to grasp quickly and effortlessly a screw pin located in the container 21 with the driven member which is detachably fastened to the drive device, for removing the screw pin from the container and screwing it into a hole 31a previously drilled into the tooth. Accordingly, the rod-shaped member 13 of the driven member 7 transmits the torque from the drive device 1 to the screw pin 9 during the insertion step and is automatically uncoupled from the screw pin when the pin is driven into the tooth for the desired depth. The engagement part 9b which remains a part of the screw pin connected to the threaded part after the screwing operation is completed, projects out of the hole 13a and provides a shaft part or head part for the screw pin 9 serving to anchor artificial material for repairing the natural tooth 31.

In FIG. 10 a sleeve-like handle 41 is shown with an axially and circumferentially extending outside surface 41a provided with knurling or the like. The sleeve-like handle 41 forms a coaxial hole 41b with an insert in one end forming a snap bolt lock 43. The driven member 7 can be inserted into the handle 41 rather than into the angle piece 5 of the drive device 1 and is detachably fastened in the handle. Accordingly, a screw pin 9 can be grasped with the handle 41 and the driven member 7 and the pin can be inserted into a tooth in the manner similar to that described above where the operation is effected using the drive device 1.

The assembly embodying the present invention can be modified in a number of ways. For example, the insertion depth of the screw pins into a tooth can be determined by means of a radially extending right-angled top face on the driven member, that is, where the stop extends perpendicularly relative to the rotational axis, or by a stop face formed at the front end of the threaded part of the screw pin, rather than using the conical stop face whereby the stop face on the front end would contact the base of the drilled hole.

Further, the clamping member can be supported on the rod-shaped member so that it is axially displaceable.

It is also possible to alter the shape of the surfaces in the slot in the engagement part and/or on the engagement projection. For example, the convex surfaces 9e could have a larger or smaller radius curvature than the concave base surface 9d. Moreover, the concave surface 9d forming the base of the slot could extend along an arc of less than 180° and the arcs of the convex side surfaces 9e could also be reduced in the length of the arc so that continuous transitions between the surfaces of the slot and the rear end face of the screw pin could be achieved. Further, the front end face 13h of the engagement, projection which is semi-circular in section, could also be reduced to an arc of less than 180°. In addition, it would be possible to form only a partial axial section of the slot in the engagement part so that it narrows toward the base of the slot. Furthermore, it would be possible to construct only the slot or only the engagement projection, at least in axial section, so that the slot or engagement projection narrows towards the base of the slot or toward the front end of the engagement projection.

Figure 11:
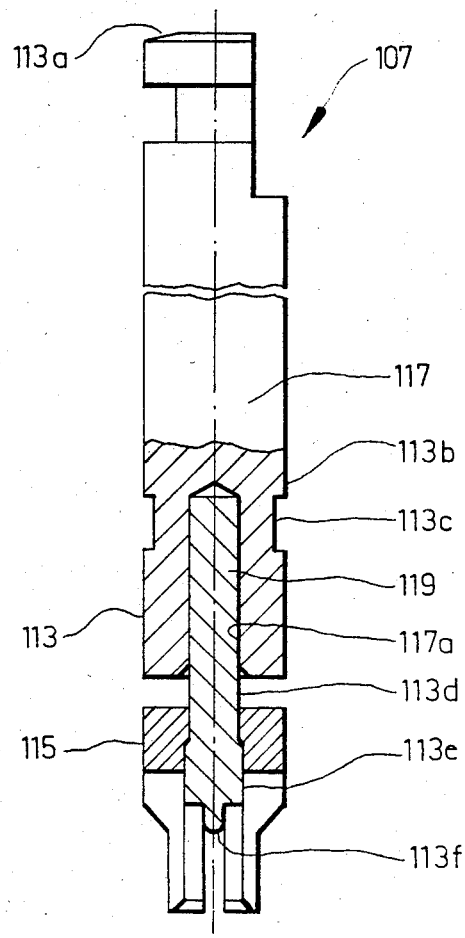
FIG. 11 is an elevational view, partly in section, of another embodiment of the driven member and its associated gripping member.

In FIG. 11 another embodiment of a driven member 107 with a rod-shaped member 113 and a gripping member 115 positioned on the rod-shaped member is displayed where the parts and surfaces of the rod-shaped member 113 have reference numerals increased by 100 with respect to the parts and surfaces of the rod-shaped member 13. While the rod-shaped member 13 is a monolithic unit it can be replaced by the rod-shaped member 113 formed of two separate parts, that is, a first part 117 made up of the rear end section 113a, and the cylindrically shaped 113b with the marking groove 113c. This first part 117 of the rod-shaped member 113 has a hole 117a formed in its front end coaxial with the axis of rotation, that is, a blind hole. The second part is a pin-shaped part 119 positioned within the hole 117a so that it is secured within the hole either by being pressed in and/or by being soldered, such as with a hard solder. The portion of the second part 119 projecting axially outwardly from the front end of the first part 117 forms a reduced diameter part 113d on which the plug-like section 113e is formed along with the engagement projection 113f of the rod-shaped member 113.

The screw pins can also be stored in an assortment tray or an open container formed as an assortment tray, rather than in a closed container.

Instead of dentine or parapulpal screw pins, screw pins can be provided to be secured in root canals of teeth and can be constructed so that they can be screwed in. Screw pins for use in root canals are usually larger than the parapulpal screw pins and their threaded parts normally have diameters greater than 1 mm, for example, in the range of 1.2 mm to 1.8 mm.

While specific embodiments of the invention have been shown and described in detail to illustrate the application of the inventive principles, it will be understood that the invention may be embodied otherwise without departing from such principles.

I claim:

1. An assembly comprising an axially elongated screw pin arranged to be screwed into a tooth and having a first end and a second end spaced apart in the axial direction, said screw pin has an axially extending threaded part extending from the first end toward the second end and an axially extending engagement part extending from the second end toward the threaded part, and a driven member for engaging said engagement part for driving said screw pin about the axis thereof so that said threaded part can be secrewed into a tooth, means for displacing said driven member out of driving engagement with said screw pin when said screw pin is fixed in a tooth, said engagement part has a slot formed axially into and being open at the second end of said screw pin, said driven member comprises an axially extending rod-like member having a first end and a second end, said rod-like member has an axially extending engagement projection at the first end thereof selectively engageable within said slot, an axially extending gripping member having a first end and a second end and said gripping member arranged to laterally enclose an axially extending portion of said rod-like member extending from the first end of said rod-like member, said gripping member has a plurality of axially extending resilient gripping tongues extending from the first end toward the second end thereof for temporarily laterally gripping and holding said engagement part, and said displacing means comprises that at least one of said slot and engagement projection has laterally spaced axially extending surfaces converging inwardly toward one another in the direction toward the respective first end of said screw pin and said rod-like member so that said engagement projection of said rod-like member moves axially out of said slot when said screw pin is fixed in a tooth.

2. An assembly, as set forth in claim 1, wherein said plot has a base surface spaced axially from the second end of said screw pin, said base surface defining a concave curve, said slot has laterally spaced axially extending side surfaces converging inwardly from the second end of said screw pin toward the base surface of said slot, each said side surface defining a convex curve and said side surfaces form a continuous curve from said base surface to the second end of said screw pin, and said engagement projection being engageable within said slot so that said engagement projection is in spaced relation with at least an axially extending part of said side surfaces.

3. An assembly, as set forth in claim 2, wherein said engagement part has an end face located at the second end of said screw pin extending transversely of the axis of said screw pin and said side surfaces of said engagement part merge continuously into said end face.

4. An assembly, as set forth in claim 2 or 3, wherein said concavely curved base surface of said slot extends along a circular arc having a maximum angular extent of 180°.

5. An assembly, as set forth in claim 4, wherein said concavely curved base surface extends for a circular arc of 180°.

6. An assembly, as set forth in claim 4, wherein each of said convexly curved side surfaces of said slot extend along a circular arc having a maximum angular extent of 90°.

7. An assembly, as set forth in claim 6, wherein the circular arc of said convexly curved side surfaces is 90°.

8. An assembly, as set forth in claim 1, 2 or 3, wherein the maximum diameter of said engagement part is larger than the diameter of said threaded part, a stop face located at the transition from said threaded part to said engagement part and said stop face projects radially outwardly from said threaded part to said engagement part so that said stop face is frusto-conically shaped and defines the insertion depth of said screw pin into a tooth.

9. An assembly, as set forth in claim 3, wherein said engagement projection has an end defining the first end of said rod-shaped member and said end has a convexly curved end face engageable with said base surface of said slot and said end face of said engagement projection extends along a circular arc having a maximum angular extent of 180°.

10. An assembly, as set forth in claim 9, wherein the angular extent of the circular arc of said end face is 180°.

11. An assembly, as set forth in claim 9, wherein said engagement projection has a pair of second side surfaces facing outwardly from said slot when said engagement projection is inserted into said slot and said second side surfaces being curved around the axis of said rod-shaped member extending along a circular arc concentric with the axis of said rod-shaped member.

12. An assembly, as set forth in claim 1, wherein said gripping member is axially displaceably secured on said rod-shaped member and is rotatable relative to said rod-shaped member, and wherein there are provided means on said rod-shaped member for limiting the axial movement of said gripping member relative to said rod-shaped member.

13. An assembly, as set forth in claim 12, wherein said means on said rod-shaped member limiting the axial movement of said gripping member are arranged to provide an axial displacement of said gripping member at least equal to the axial depth of said slot from the second end of said screw pin.

14. An assembly, as set forth in claim 1, comprising a container arranged to hold at least one said screw pin, at least one screw pin carrier located within said container, surfaces within said carrier defining an axially extending hole for receiving one said screw pin and said hole having a first hole section arranged to receive said threaded part of said screw pin and a second hole section arranged to receive said engagement part of said screw pin, and the diameter of said second hole section is at least equal to the diameter of said first end of said gripping member so that the first end of said gripping member can be inserted into said second hole section whereby said gripping tongues can engage and hold said engagement part of said screw pin located within said hole.

15. An assembly, as set forth in claim 1, wherein said rod-shaped member is a monolithic member.

16. An assembly, as set forth in claim 1, wherein said rod-shaped member comprises a first axially extending section having an axially extending blind hole therein and a second axially extending section engageable within said blind hole and arranged to project outwardly from said first section and said second section forming said engagement projection.

17. An assembly, as set forth in claim 1, wherein the axial depth of said slot in the second end of said screw pin is less than the axial length of said engagement projection on said rod-shaped member.

18. An assembly, as set forth in claim 17, wherein said engagement projection having a pair of axially extending side surfaces disposed in parallel and arranged to be located at least in part within said slot when said engagement projection is fully inserted into said slot.

19. An assembly, as set forth in claim 1, wherein said gripping tongues on said gripping member are inclined slightly inwardly toward the first end of said gripping member so that when the engagement part of said screw pin is gripped by said gripping tongues said gripping tongues are displaced radially outwardly at the first end of said gripping member so that the outside surfaces of said tongues adjacent the first end of said gripping member define a cylindrical surface.

20. An assembly, as set forth in claim 19, wherein said gripping member has a first axially extending section extending from the first end thereof toward the second end thereof, a second axially extending section extending from the second end thereof toward the first end thereof, and a third axially extending section forming a transition section between said first section and said second section, said first section having a smaller outside diameter than the outside diameter of said second section and said third section having a frusto-conically shaped outside surface extending between said first section and said second section, and said second section having a first inside diameter extending from the second end of said gripping member slightly smaller than the remaining inside diameter of said second section.

21. An assembly, as set forth in claim 20, wherein said gripping tongues extend axially through said first axial section and third axial section of said gripping member into said second axial section so that the ends of said gripping tongues spaced from the first end of said gripping member are disposed in axially spaced relation from the second end of said gripping member.

22. An assembly, as set forth in claim 1, comprising means arranged to hold at least one said screw pin, at least one screw pin carrier located within said means, surfaces within said carrier defining an axially extending hole for receiving one said screw pin and said hole having a first hole section arranged to receive said threaded part of said screw pin and a second hole section arranged to receive said engagement part of said screw pin, and the diameter of said second hole section is at least equal to the diameter of said first end of said gripping member can be inserted into said second hole section whereby said gripping tongues can engage and hold said engagement part of said screw pin located within said hole.

23. An assembly, as set forth in claim 22, wherein said means comprises a container and a cover for closing said container.

24. An assembly, as set forth in claim 22, wherein said means comprises an open topped assortment tray.

* * * * *

UNITED STATES PATENT AND TRADEMARK OFFICE
CERTIFICATE OF CORRECTION

PATENT NO. : 4,553,942
DATED : November 19, 1985
INVENTOR(S) : Franz Sutter

It is certified that error appears in the above-identified patent and that said Letters Patent is hereby corrected as shown below:

In the heading of the Patent it should read as follows:

[73] Assignee: Institut Straumann AG
Waldenburg, Switzerland

Signed and Sealed this

Twenty-eighth Day of October, 1986

[SEAL]

*Attest:*

DONALD J. QUIGG

*Attesting Officer*     *Commissioner of Patents and Trademarks*